United States Patent

Diaz Cabañas et al.

[11] Patent Number: 6,077,498
[45] Date of Patent: Jun. 20, 2000

[54] ZEOLITE ITQ-1

[75] Inventors: María José Diaz Cabañas; Miguel Angel Camblor Fernandez; Catalina Corell Martires; Avelino Corma Canos, all of Valencia, Spain

[73] Assignees: Consejo Superior Investigaciones Cientificas, Madrid; Universidad Politecnica de Valencia, Valencia, both of Spain

[21] Appl. No.: 08/875,302
[22] PCT Filed: Nov. 19, 1996
[86] PCT No.: PCT/ES96/00218
 § 371 Date: Oct. 7, 1997
 § 102(e) Date: Oct. 7, 1997
[87] PCT Pub. No.: WO97/19021
 PCT Pub. Date: May 29, 1997

[30] Foreign Application Priority Data

Nov. 23, 1995 [ES] Spain ................................. 9502306

[51] Int. Cl.[7] ................................................ C01B 39/46
[52] U.S. Cl. .......................... 423/702; 423/705; 423/706; 423/707; 423/709; 423/718
[58] Field of Search ....................... 423/702, 703, 423/705, 706, 707, 709, 718, 326, 328.2, 329.1; 208/111, 120, 310 Z; 585/666, 671, 820

[56] References Cited

U.S. PATENT DOCUMENTS 4,439,409 3/1984 Puppe et al. .
4,826,667 5/1989 Zones et al. .............................. 423/718
4,954,325 9/1990 Rubin et al. ............................. 423/718
5,236,575 8/1993 Bennett et al. .......................... 423/718
5,362,697 11/1994 Fung et al. .............................. 423/718

FOREIGN PATENT DOCUMENTS 0293032 11/1988 European Pat. Off. .

Primary Examiner—Mark L. Bell
Assistant Examiner—David Sample
Attorney, Agent, or Firm—Klauber & Jackson

[57] ABSTRACT

The present invention relates to a microporous crystalline material of zeolitic nature, called ITQ-1A, to the process for its preparation and its use in processes of separation and transformation of organic compounds. In the roasted and anhydrous stage, the chemical composition of the material corresponds to the empirical formula: $x(M_{1/n}XO_2)$: $yYO_2:SiO_2$, wherein x has a value smaller than 0.02 and may equal 0: y has a value smaller than 0.04 and may equal 0: m is $H^+$ or an inorganic cation with the charge +n: X is a chemical element with an oxidation status +3 (Al, Ga, B, Cr) and Y is a chemical element with an oxidation status +4 (Ti, Ge, V). When x=0 and y=0, the material may be described as a new polymorphe form of microporous silica. The material of this invention is characterized also by its X ray diffraction pattern. The process for the preparation of said zeolite is characterized by the use of one or a plurality of organic additives in a reaction mixture which is crystallized through heating.

12 Claims, 2 Drawing Sheets

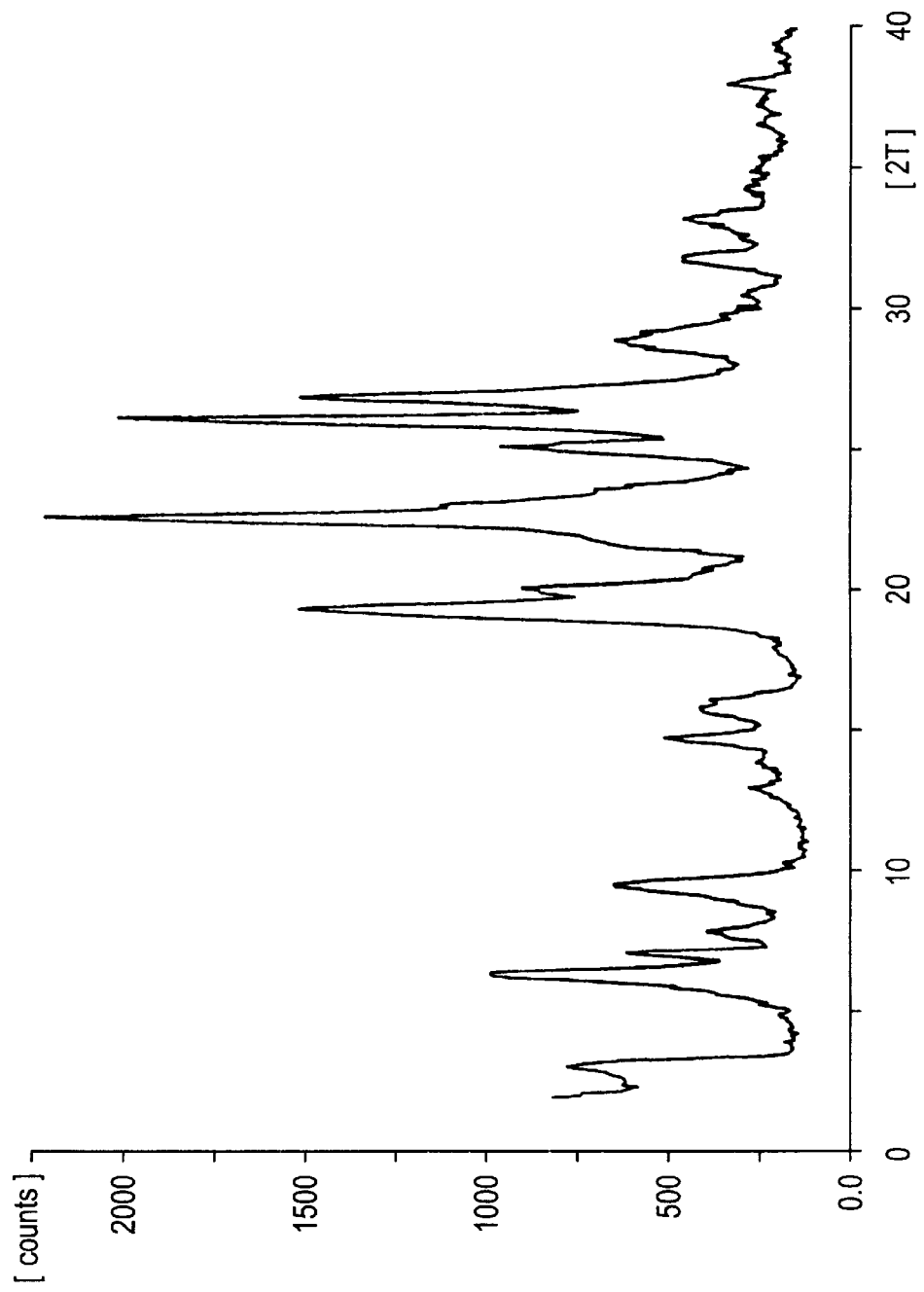

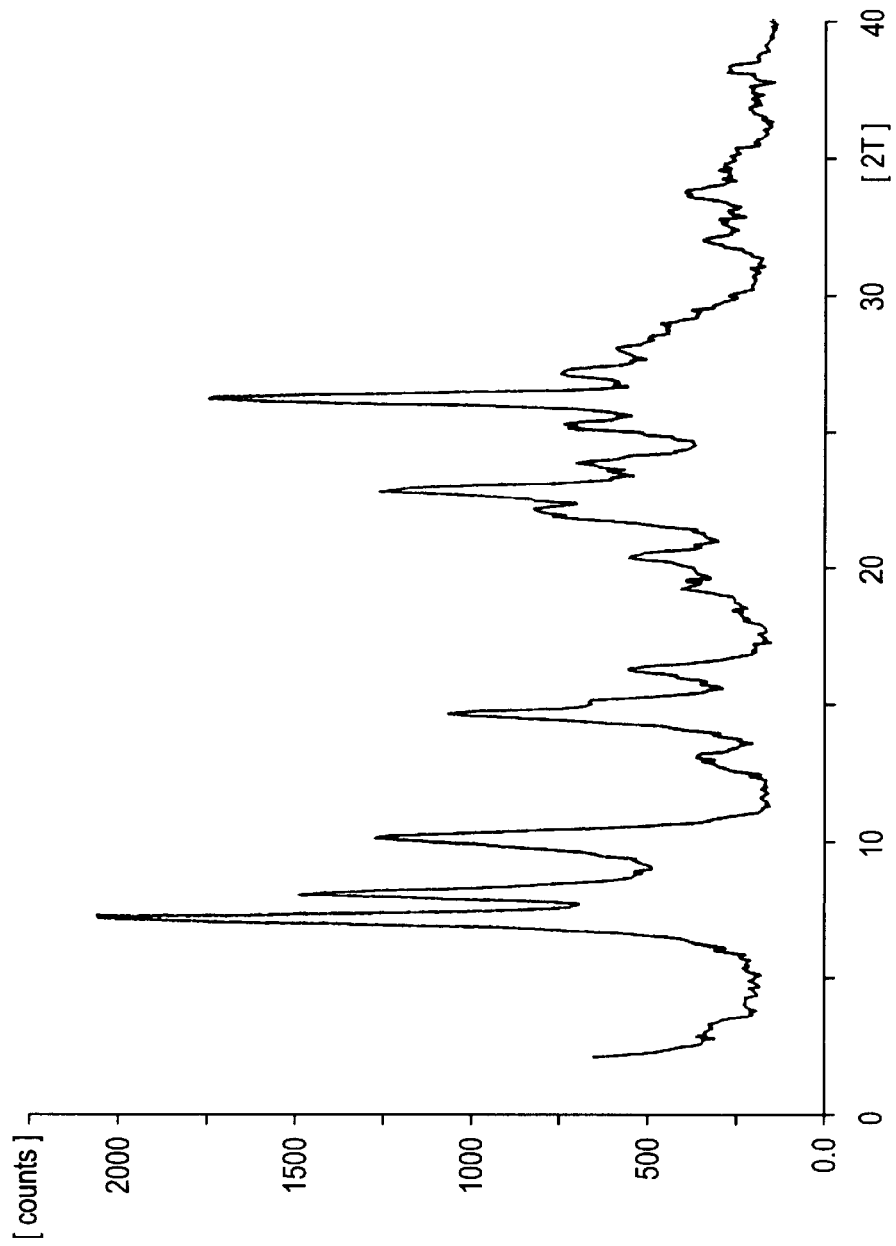

ZEOLITE ITQ-1

FIELD OF THE ART

Crystalline microporous materials

BACKGROUNDS

The zeolites are microporous crystalline materials of variable composition, characterized by a crystal lattice of $TO_4$ tetrahedrons (where T represents atoms with formal oxidation status of +3 or +4, as for example Si, Ti, Al, Ge, B, Ga, . . . ) that share all their vertexes causing a tridimensional structure which contains channels and/or cavities of molecular dimentions. When any of the T atoms present an oxidation status smaller than +4, the crystal lattice which is formed, presents negative charges which are compensated by means of the presence in the channels or cavities of organic or inorganic cations. In said channels and cavities, organic and $H_2O$ molecules may also be housed, due to which, in general, the chemical composition of the zeolites may be represented by means of the following empirical formula:

$$x(M_{1/n}XO_2) \colon yYO_2 \colon zR \colon wH_2O$$

where, M is one or various organic or inorganic cations of +n charge; x is one or various trivalent elements; Y is one or various tetravalent elements, generally Si; and R is one or various organic substances. Though the nature of M, X, Y and R and the values of x, y, z, and w may, in general, be varied by means of postsynthesis treatments, the chemical composition of a zeolite (as synthetized or after its roasting) possesses a characteristic range of each zeolite and of its method of obtention.

On the other hand, a zeolite is also characterized by its crystalline structure, which defines a system of channels and cavities and which cause a diffraction pattern of specific X-rays. In this manner, the zeolites are differentiated from each other by their chemical composition range plus their X ray diffraction pattern. Both characteristics (crystalline structure and chemical composition) also determine the physio-chemical properties of each zeolite and their applicability in different industrial processes.

DESCRIPTION OF THE INVENTION

The present invention relates to a crystalline microporous material of zeolitic nature, called ITQ-1, to its method of obtention and to its applications.

Such a material is characterized by its chemical composition and by its X ray difraction pattern. In its anhydrous and roasted form, the chemical composotion of ITQ-1 may be represented by means of the empirical formula $$x(M_{1/n}XO_2) \colon yYO_2 \colon SiO_2,$$

wherein x possesses a value smaller than 0.02, and may equal zero; y has a value smaller than 0.04, and may likewise equal zero; M is H+ or an inorganic cation with charge +n; X is a chemical element with oxidation status +3 (as, for example, Al, Ga, B, Cr) and Y is a chemical element with oxidation status +4 (as for example, Ti, Ge, V). When x=0 and y=0, the material may be described as a new polymorphe form of silica ($SiO_2$) characterized by its microporous character. In a preferred embodiment of the present invention, ITQ-1 has the composition, in roasted and anhydrous stage $$x(HXO_2) \colon SiO_2$$

wherein X is a trivalent element and x possesses a value smaller than 0.02 and may equal zero, in which case, the material may be described by means of the formula $SiO_2$. However, depending on the method of synthesis and on its roasting or subsequent treatments, the existance of defects in the crystal lattice is possible, which are manifested by the presence of Si—OH groups (silanoles). Said defects have not been included in the previous empirical formulas.

BRIEF DESCRIPTION OF THE DRAWINGS

FIG. 1 Diffraction pattern of ITQ-1.

FIG. 2 Diffraction patter as a result of roasting.

The X ray diffraction pattern of ITQ-1, such as is synthesized, obtained by the powder method using a variable slit of divergence (constant irradiated area), is characterized by the following interplanar spaced values (d) and relative intensities ($I/I_o$):

TABLE I

| d (Å) | $I/I_o$ (%) |
|---|---|
| 26.8 | 25 |
| 13.5 | 40 |
| 12.1 | 20 |
| 11.1 | 10 |
| 9.17 | 10 |
| 7.33 | 5 |
| 6.85 | 10 |
| 6.31 | 5 |
| 5.98 | 20 |
| 5.62 | 15 |
| 5.49 | 10 |
| 4.64 | 50 |
| 4.55 | 60 |
| 4.42 | 35 |
| 4.11 | 20 |
| 3.94 | 100 |
| 3.84 | 45 |
| 3.75 | 20 |
| 3.55 | 40 |
| 3.41 | 90 |
| 3.31 | 65 |
| 3.09 | 20 |
| 3.05 | 20 |
| 2.92 | 5 |
| 2.82 | 15 |
| 2.69 | 10 |
| 2.62 | 5 |

Such a diffraction pattern is represented in FIG. 1 (Kα radiation of Cu). The relative positions and intensities of the peaks depend in certain measure on the chemical composition of the material (the pattern represented in Table I and FIG. 1 refers to the material with a lattice comprised exclusively of silicon oxide, $SiO_2$ and synthetized using a quaternary ammonium cation as structure director agent). Also, the roasting causes significant changes in the X-ray diffraction pattern, due to which in Table II and FIG. 2, the ITQ-1 diffraction pattern is represented as roasted, of composition $SiO_2$.

TABLE II

| d (Å) | $I/I_o$ (%) |
|---|---|
| 25.4 | 5 |
| 12.2 | 100 |
| 11.0 | 70 |
| 8.80 | 60 |
| 6.84 | 10 |
| 6.16 | 55 |
| 5.95 | 25 |
| 5.53 | 25 |

TABLE II-continued

| d (Å) | I/I₀ (%) |
|---|---|
| 5.23 | 5 |
| 4.93 | 5 |
| 4.65 | 10 |
| 4.38 | 20 |
| 4.09 | 30 |
| 4.03 | 35 |
| 3.88 | 50 |
| 3.74 | 30 |
| 3.55 | 30 |
| 3.41 | 100 |
| 3.28 | 30 |
| 3.19 | 20 |
| 3.11 | 15 |
| 2.81 | 10 |
| 2.75 | 6 |
| 2.67 | 15 |
| 2.56 | 5 |

Such an X ray diffraction pattern is very similar to the zeolites called PSH-3 (Eur. Pat. 64205), MCM-22 (U.S. Pat. No. 4,954,325 and U.S. Pat. No. 5,173,281), MCM-49 (WO 92/22498), SSZ-25 (Eur. Pat. 231860) and ERB-1 (Eur. Pat. 293032), which suggests a certain structural similarity or even isomorphism of all the indicated materials. However, the chemical composition of ITQ-1, characterized by a high relation (Si+Y)/X (where Y is a different tetravalent element of Si and X the trivalent element of the crystal lattice) distinguishes the material of the present invention from other said materials and provides its special physio-chemical characteristics. Thus ITQ-1 is characterized in that it has a relation (Si+Y)/X greater than 50, capable even of being presented as a polymorphic form of silica. On the other hand, for the rest of said materials, examples are not found in the scientific literature or that of synthesis patents with relations Si/X greater than 50, this relation normally being in the range of 10–40.

The present invention relates also to the method of preparation of ITQ-1. It comprises a heat treatment at temperatures between 80 and 200° C., preferably between 130 and 180° C., of a reaction mixture which contains a source of $SiO_2$ (as, for example, tetraethylortosilicate, soloidal silica, amorphous silica), an organic cation in the form of hydroxide, preferably of N, N,N trimethyl-1-adamantammonium hydroxide ($C_{13}H_{24}NOH$, I) or N,N,N trimethyl-2-adamantammonium hydroxide ($C_{13}H_{24}NOH$, II) and water. In the reaction mixture it is possible to add advantageously, primary or secondary amines, as for example hexamethylenimine ($C_6H_{12}NH$, III), cyclohexylamine ($C_6H_{11}NH_2$), cyclopenthylamine ($C_5H_9NH_2$), cycloheptylamine ($C_7H_{13}NH_2$), heptamethylenimine ($C_7H_{14}NH$), homopiperazine ($C_5H_{10}(NH)_2$) or mixtures of the same. The relation amines/(quaternary ammonium) (wherein quaternary ammonium is any of the isomers I or II or a mixture of both) is comprised in the range 0 to 20, preferably in the range 0 to 10, more preferably in the range 0 to 5. Additionally, when a proportion of amines is used which permits the obtention of sufficiently high alkalinities, the cations N,N,N-trimethyl-1-adamantammonium and N, N, N-trimethyl-2-adamantammonium may be used, totally or partially, in the form of a different salt to hydroxide, for example in the form of halide.

It is optionally possible to add a source of other tetravalent element Y and/or trivalent X, pre ferably Ti or Al. The addition of said element may be performed prior to the heating of the reaction mixture or in an intermediate time during said heating. On occasions it may also be convenient to introduce at any moment of the preparation crystals of ITQ-1 (up to 15% in weight as regards the inorganic oxid group, preferably up to 10% in weight) as promoters of the crystallization (sowing). The composition of the reaction mixture in the form of oxides responds to the general formula $$rR_2O:aRN:xXO_2: yYO_2: SiO_2:wH_2O$$

where X is one or various trivalent elements, preferably Al; Y is one or various tetravalent elements; R is an organic cation, preferably N,N,N-trimethyl-1-adamantammonium or N,N,N-trimethyl-2-adamantammonium; RN is a primary or secondary amine, preferably hexamethylenimine, heptamethylenimine, hompiperazine, cyclopenthylamine, cyclohexylamine or cyclohepthylamine, preferably hexamethylenimine; and the values of r, a, x, y and w are in the ranges r=0.05–0.25, preferably 0.1–0.2
a/r=0–20, preferably 0–5
x=0–0.033
y=0–0.05
w=4–100, preferably 5–50, more preferably 25–50

The heat treatment of the reaction mixture may be performed statically or with agitation of the mixture. Once the crystallization is ended, the solid product is separated and dried. The subsequent roasting at temperature between 400 and 650° C., preferably between 450 and 600° C., produces the decomposition of the organic cation (and amines) occluded in the zeolite and frees the zeolitic channels.

Said synthesis method of the zeolite ITQ-1 has the particularity that it is not introduced in the alkaline cations reaction medium (except possible impurities contained in some cases in the reactives), on the contrary to what happens in the preparative methods of PSH-3, MCM-22, MCM-49, SSZ-25 and ERB-1 described in the previously indicated patents. The consequence of this is that the organic cation R is the only cation which compensates lattice charges when the zeolite contains a trivalent element in its crystal lattice. Therefore, a simple roasting in order to decompose the organic cation leaves the zeolite in acid form, without the need to resort to processes of cationic interchange. Also, the absence of alkaline cations in the reaction mixture permits to synthesize the material containing elements such as the Ti(1V), which would not be possible to introduce in the lattice in the presence of said cations (see for example, M. A. Camblor, A. Corma, J. Pérez-Pariente, Zeolites, vol. 13, 82–87, 1993). Once roased, the material responds, in consequence to the general formula $$x(HXO_2):yYO_2:SiO_2$$

where x has a value smaller than 0.02, and may equal zero; y has a value smaller than 0.04, and may likewise equal zero; X is a chemical element with oxidation status +3 and Y is a chemical element with oxidation status +4.

EXAMPLES

Example 1

The example illustrates the preparation of ITQ-1 purely silica, using N,N,N-trimethyl-1-adamantammonium as structure director organic agent.

To 5.970 g of water, 10.44 g of a solution 0.5M of N,N,N-trimethyl-1-adamantammonium hydroxide was added. Next, 1.22 g of silica (Aerosil 200, Degussa) was added, simultaneously agitating the mixture. Said mixture is heated at 150° C. under agitation of 60 rpm during 14 days in a steel PTFE interiorly lined autoclave. After cooling the reactor, it is filtered and the solid washed with distilled water. The white product obtained is dried at 100° C. Said product (1.36 g) presents an X ray diffraction pattern, essentially coincident with that collected in Table I and FIG. 1. After roasting at 540° C. during 2 hours, the X ray diffraction pattern coincides with that collected in Table II and FIG. 2. The chemical analysis of the material roasted by atomic absorption spectroscopy reveals, within the detection limits of the art, and the experimental error, that the product obtained is silica ($SiO_2$). Adsorption measures of $N_2$ indicate a surface area of 264 $m^2$/g (B.E.T. method) and a micropore volume of 0.08 cc/g.

Example 2

This example illustrates the preparation of ITQ-1 containing silicon and aluminium in its composition, using the same structure director organic compound as in example 1. Then 0.006 g of metallic Al is dissolved in 47.249 g of water and 57.035 g of a solution of 0.52 M of N,N,N-1-trimethyladamantammonium hydroxide. Next add 7.18 g of $SiO_2$ (Aerosil 200, Degussa) and agitate. The crystallization is performed at 150° C. under agitation (60 rpm). After 21 days, ITQ-1 with high crystallinity is obtained and a molar relation of Si/AL=464.

Example 3

This example illustrates the advantageous use of amines in the ITQ-1, purely silica synthesis medium.

To 22.965 g of water was added 45.785 g of a 0.44M N,N,N-1-trimethyladamantammonium hydroxide solution and 2.500 g of hexamethylenimine. Next was added 4.88 g of silica (Aerosil 200, Degussa) simultaneously agitating the mixture. Said mixture is heated at 150° C. under agitation (60 rpm) during 9 days. The white product obtained presents the diffraction pattern of FIG. 1, and an improved definition of peaks, better than the one shown in example 1. After roasting at 540° C., during 2 hours, the product presents the diffraction pattern of FIG. 2, and an improved definition of the peaks than the roasted sample of example 1. The chemical analysis of the material roasted by means of atomic absorption spectorscopy reveals, within the detection limits of the art and the experimental error, that the product obtained is silica ($Sio_2$). Adsorption measures of $N_2$ indicates a surface area of 409 $m^2$/g (B.E.T. method) and a microporous volume of 0.15 cc/g. The use of an amine quaternary ammonium cation mixture consequently permits the shortening of the synthesis time and the obtention of the material with higher crystallinity, improved stability when roasting, and improved adsorption characteristics.

Example 4

This example illustrates the preparation of ITQ-1 with high Al contents.

A 28.57 g of a N,N,N-1-trimethyladamantammonium hydroxide 0.88M solution is mixed with 0.1148 g of alumina (Pural SB) and 36.27 g of water, and agitated during 4 hrs. Next 12.66 g of colloidal silica (Ludox AS-40) is added and agitated during 2 hrs. The mixture is crystallized at 150° C. under agitation (60 rpm). After 28 days, a solid product is obtained with a pattern essentially coincident to that of FIG. 1.

Example 5

This example illustrates the preparation of ITQ-1 with a high Al content using a mixture of quaternary ammonium cation and amine.

A 51.10 g of a N,N,N-1-trimethyladamantammonium hydroxide 0.46 M solution is mixed with 0.,108 g of alumina (Pural SB), 2.91 g of hexamethylenimine and 9.082 g of water, and agitated during 4 hrs. Next add 11.80 g of colloidal silica (Ludox AS-40) and agitated during 2 hrs. The mixture is crystallized at 150° C. under agitation (60 rpm). After 11 days, a solid product is obtained with a pattern essentially coincident to that of FIG. 1. A chemical analysis of the solid reveals a molar relation of Si/Al=61.7.

We claim:

1. A method for synthesizing a microporous crystalline material of zeolitic nature with an X ray diffraction pattern which is substantially concordant with that established in Tables I and II for the material as synthesized and after roasting, respectively, and with a chemical composition in roasted and anhydrous state represented by the empirical formula $x(M_{1/n}XO_2):yYO_2:SiO_2$ wherein x has a value smaller than 0.02; y has a value smaller than 0.04; M is H+ or a cation with charge +n; X is a chemical element with oxidation status of +3 and Y is a chemical element with oxidation status +4, and wherein the molar ratio (Si+Y): X is higher than 50, wherein a reaction mixture having a composition, in terms of oxide molar ratios. of $X_2O_3/SiO_2$=0–0.033

$ROH/SiO_2$=0.1–0.5

$YO_2/SO_2$=0–0.05

$H_2O/SiO_2$=4–100 wherein

X is at least one trivalent element,

Y is at least one tetravalent element other than Si;

R is hydroxide of a R+ organic cation, the reaction mixture containing a source of $SiO_2$, hydroxide of a R+ organic cation, a source of one or various tetravalent elements other than Si when Y is present, a source of one or various trivalent elements, and water, is subjected to heating with or without agitation to a temperature between 80 and 200° C., until its crystallization is obtained, whereby no source of alkaline earth metal nor a source of alkali metals is added to the reaction mixture.

2. A method according to claim 1, wherein the composition of the reaction mixture is $X_2O_3/SiO_2$=0–0.03

$ROH/SiO_2$=0.1–0.5

$H_2O/SiO_2$=4–100.

3. A method according to claim 1, wherein the composition of the reaction mixture is $ROH/SiO_2$[0, 1]0.1–0.5

$YO_2/SiO_2$=0–0.05

$H_2O/SiO_2$=4–100.

4. A method according to claim 1, wherein an amine selected from primary or secondary RN amine is added to the reaction mixture in a RN/R+ ratio lower than 20 and in which R+ quaternary ammonium cation is added as salt.

5. A method according to claim 1, wherein a crystalline material is added to the reaction mixture as crystallization promoter in a quantity between 0.01 and 15% by weight of total added silica.

6. A method according to claim 1, wherein a source of a tetravalent element source being different from Si, or a source of a trivalent element, is introduced in an intermediate stage when the reaction mixture is heated.

7. A method according to claim 1, wherein the temperatures is between 130 and 180° C.

8. A method according to claim 1, wherein the ROH/SiO$_2$ ratio is 0.2–0.4.

9. A method according to claim 1, wherein the H$_2$O/SiO$_2$ ratio is 5–50.

10. A method according to claim 1, wherein the H$_2$O/SiO$_2$ ratio is 25–50.

11. A method according to claim 4, wherein the amine is selected from the group consisting of hexamethylenimine, heptamethylenimine, homopiperazine, cyclopenthylamine, cyclohexylamine, cyclohepthylamine and mixtures thereof.

12. A method according to either of claims 1 or 4, wherein the R+ quaternary ammonium cation is selected from the group consisting of N,N,N-1-trimethyladamantammonium or N,N,N-2-trimethyladamantammonium, and mixtures thereof.

* * * * *